United States Patent [19]

Banys et al.

[11] Patent Number: 5,425,376
[45] Date of Patent: Jun. 20, 1995

[54] METHOD AND APPARATUS FOR OBTAINING A BIOPSY SAMPLE

[75] Inventors: Algis R. Banys; George H. Middle, both of Reno, Nev.

[73] Assignee: Sofamor Danek Properties, Inc., Memphis, Tenn.

[21] Appl. No.: 119,020

[22] Filed: Sep. 8, 1993

[51] Int. Cl.6 .............................................. A61B 5/00
[52] U.S. Cl. .................................................... 128/753
[58] Field of Search ............................. 128/751–754; 606/167, 170

[56] References Cited

U.S. PATENT DOCUMENTS

| | | | |
|---|---|---|---|
| 2,816,552 | 12/1957 | Hoffman | 128/305 |
| 2,850,007 | 9/1958 | Lingley | 128/754 |
| 3,400,708 | 9/1968 | Scheidt | 128/2 |
| 3,477,423 | 11/1969 | Griffith | 128/754 |
| 3,512,519 | 5/1970 | Hall | 128/2 |
| 3,605,721 | 9/1971 | Hallac | 128/2 B |
| 3,990,453 | 11/1976 | Douvas et al. | 128/305 |
| 4,441,509 | 4/1984 | Kotsifas et al. | 128/757 |
| 4,681,123 | 7/1987 | Valtchev | 128/753 |
| 4,708,147 | 11/1987 | Haaga | 128/753 |
| 4,735,215 | 4/1988 | Goto et al. | 128/754 |
| 4,757,826 | 7/1988 | Abdulhay | 128/757 |
| 4,765,332 | 8/1988 | Fischell et al. | 128/24 A |
| 4,825,865 | 5/1989 | Zelman | 128/303.1 |
| 5,047,008 | 9/1991 | de Juan et al. | 128/751 |
| 5,178,625 | 1/1993 | Groshong | 606/159 |
| 5,287,857 | 2/1994 | Mann | 128/753 |

Primary Examiner—Max Hindenburg
Attorney, Agent, or Firm—Woodard, Emhardt, Naughton, Moriarty & McNett

[57] ABSTRACT

A tool is disclosed, for taking a biopsy sample, having a needle attached to a syringe, with an opening in the side of the needle, which can be selectively covered by a cannula slidably mounted over the needle. The cannula can be locked into place on the needle, and the plunger of the syringe can be spring loaded to draw a sample into the syringe upon release of a latch. A method is also disclosed for taking a biopsy sample by sliding a cannula over a needle, inserting the cannula and needle into the tissue to be sampled, partially withdrawing the cannula from the needle to expose a lateral opening in the needle, maneuvering a sample of the tissue into the opening, cutting the sample from the tissue, and drawing the sample out through the needle.

15 Claims, 2 Drawing Sheets

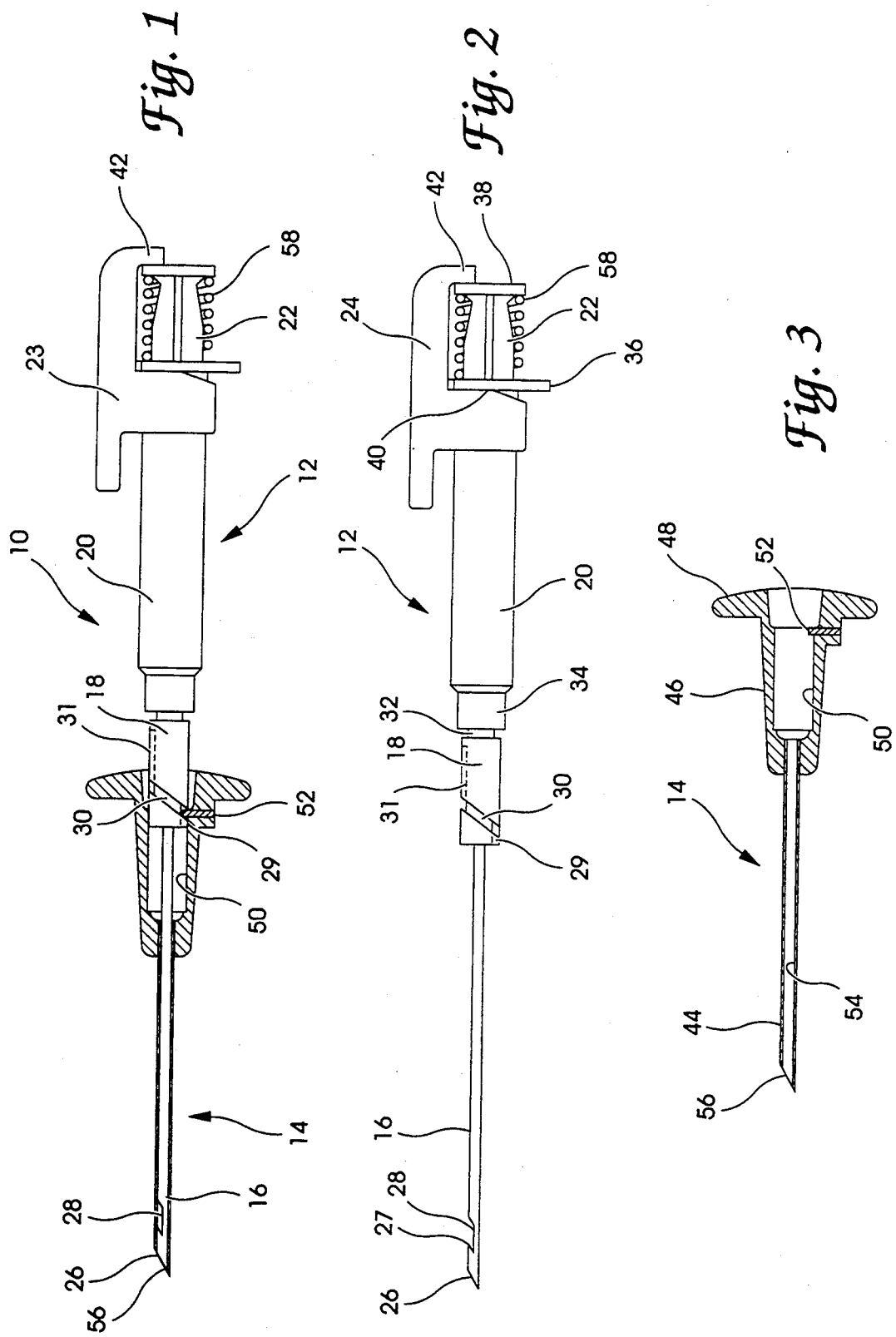

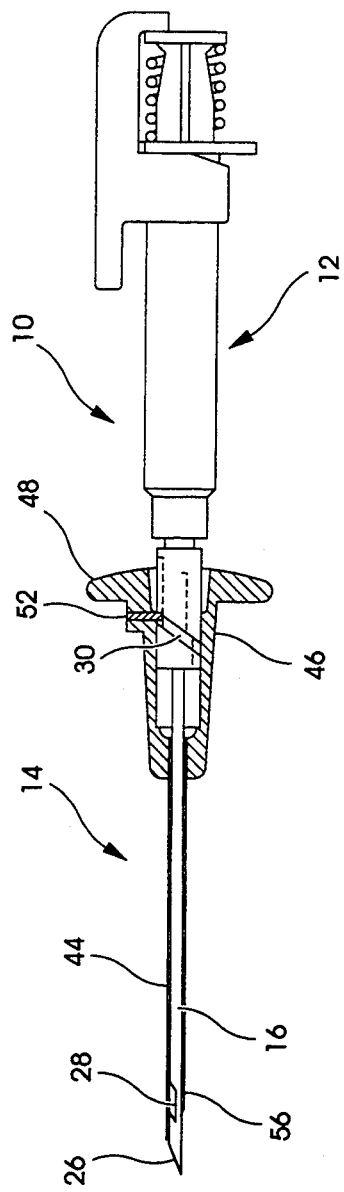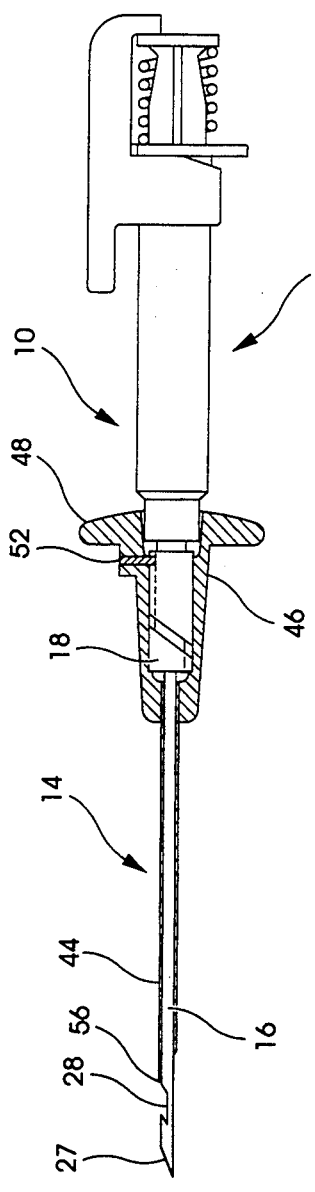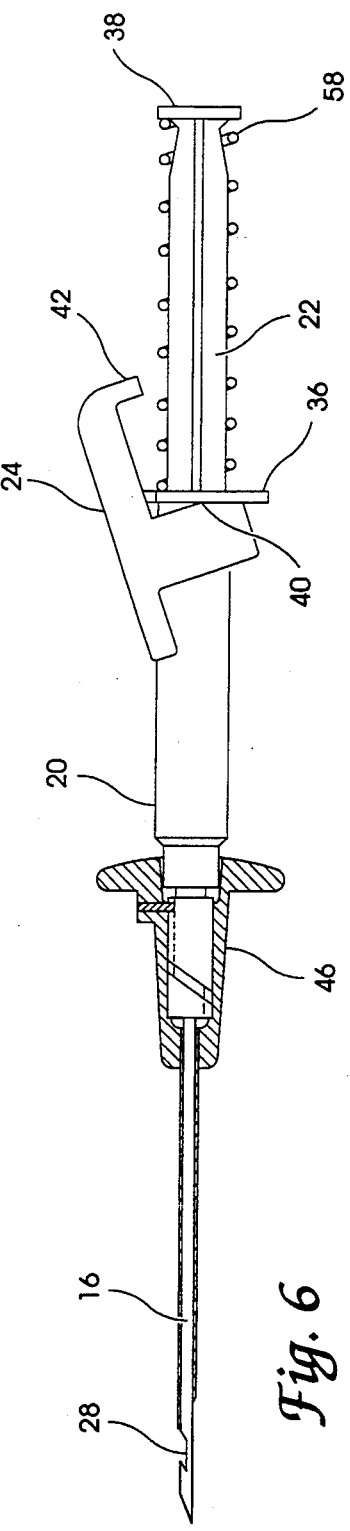

METHOD AND APPARATUS FOR OBTAINING A BIOPSY SAMPLE

TECHNICAL FIELD

The method and apparatus of this invention are in the field of taking samples of selected tissue for examination outside the body of a patient. Specifically, the method and apparatus of this invention provide a means for inserting a sampling needle into the target tissue, with the opening in the needle being covered by a cannula. The cannula can be withdrawn to expose the opening to the tissue, and a sample obtained, avoiding contamination of the sample with unwanted tissue.

BACKGROUND OF THE INVENTION

In the diagnosis and treatment of disease, it is often necessary or desirable to take a sample of selected tissue from a living patient, called a biopsy sample, in order to analyze the sample as an aid to diagnosis and treatment of the disease. Such a procedure can be useful in diagnosing and treating various forms of cancer, as well as other diseases in which a localized area of affected tissue can be identified. In particular, a disease associated with the formation of a tumor often indicates the desirability of taking a sample of the affected tissue.

In some cases, the tissue sample can be directly excised from the affected area, if the area is easily accessible, and highly invasive surgical procedures are not necessary. In other cases, the affected area is not readily accessible, and the biopsy sample should be taken, if possible, by means that minimize the physical trauma inflicted upon the intervening tissues that surround the affected area or target tissue. The biopsy sample procedure in such cases is typically performed by inserting a hollow biopsy needle through the intervening tissue into the target tissue to be sampled. Alternatively, a stylet with a notch in its side can be inserted, followed by a cutting cannula over the stylet. It is also possible to use the biopsy needle procedure in cases where the target tissue is easily accessible, to minimize trauma to the target tissue.

Once the biopsy needle has been inserted into the target tissue, current procedure involves the withdrawal of sample tissue through the needle by placing a suction on the needle, such as with a syringe. As mentioned above, if the notched stylet is used, it is inserted into the target tissue, then the cutting cannula is inserted over the stylet to cut the sample tissue off in the notch of the stylet. These procedures and the associated apparatus suffer from several disadvantages. First, since the biopsy needle is hollow and open at the end, pushing the needle through intervening tissues to the target area results in the accumulation of unwanted tissue in the needle, which can interfere with or complicate sample analysis.

Second, the tissue which is obtained as a sample is drawn into the needle by suction or cut by the cutting cannula, and the presently known methods require the use of two hands by the surgeon. Even using two hands, it is difficult to apply a uniform suction, quickly, through the full stroke of the syringe plunger. If suction is not applied quickly and uniformly, system leakage can interfere with obtaining a complete sample of desired tissue. Third, the size of the tissue sample is limited by the size of the opening in the leading end of the biopsy needle. Fourth, the maneuvering of the biopsy needle or stylet and operation of the associated syringe plunger or cutting cannula can be very difficult, and it typically requires the use of two hands by the surgeon. If an inadequate sample is obtained, repeated samples must be taken, increasing trauma to the patient.

Finally, the open end of a biopsy needle or the projecting edge of a cutting cannula can tear the surrounding tissue unnecessarily.

It is an object of this invention to provide an apparatus, and method of taking a biopsy sample, which requires the use of only one hand by the physician, which obtains a relatively large, uncontaminated, cleanly cut sample. It is a further object of this invention to provide a biopsy tool having a needle with a closed distal end and a lateral opening which can be selectively blocked by a cannula movably mounted on the needle, and having a means for drawing a rapid, uniform suction to pull the sample through the needle.

It is a still further object of this invention to provide a biopsy tool, having a needle with a closed distal end and a lateral opening near the distal end, having a cannula movably mounted over the needle, with its cutting edge aligned with a flat surface on the leading end of the needle, to selectively block the lateral opening, having a means for selectively locking the cannula in place on the needle, and having a means for drawing a rapid, uniform suction on the needle. It is a still further object of this invention to provide a method for obtaining a biopsy sample, by covering a needle with a cannula, inserting the needle and cannula to the affected area, moving the cannula relative to the needle to expose a lateral opening in the needle, maneuvering sample tissue into the lateral opening, cutting sample tissue from the affected area, and steadily but quickly drawing the sample tissue through the needle.

Finally, it is an additional object of this invention to provide a biopsy tool which is relatively cost effective to make and relatively easy to use.

SUMMARY OF THE INVENTION

One embodiment of this invention, given for exemplary purposes only, is a biopsy tool, and a method of use thereof, which incorporates a hollow needle having a closed distal end and having a lateral opening in the side of the needle near its distal end. The lateral opening can be relatively large, as compared to the size of the bore of the needle, and it can have a sharp edge along at least one edge of the opening. The tool also incorporates a hollow cannula which is slidably mounted over the needle, so that the cannula can be advanced or withdrawn relative to the needle, to selectively block or expose the lateral opening in the needle. The cannula can also have a sharp edge on its distal end, so that advancing the cannula along the needle can cut off the tissue sample that has been maneuvered into the lateral opening of the needle. The sharp edge on the end of the cannula can be shaped to perfectly align with the closed front end of the needle during insertion into the target tissue, to minimize trauma to the surrounding tissue.

The needle is mounted on a luer barrel which can be attached to a syringe. The syringe has a plunger within the syringe barrel, spring loaded in the outward or rearward direction, relative to the syringe. The plunger can be locked in the fully inserted position within the syringe, by a releasable latch attached to the syringe.

The luer barrel, or locking barrel, also is used to lock the cannula in a desired longitudinal position relative to the needle. To accomplish this locking feature, a guide groove is formed in the external surface of the locking barrel. This groove has three segments. The first segment extends longitudinally, from the forward end of the locking barrel, only a short distance along the barrel. The second segment follows a helical path half way around the perimeter of the barrel. The third segment extends longitudinally along the locking barrel, on the opposite side of the barrel from the first segment.

The cannula has a handle or hub which has an internal cavity which fits over the locking barrel when the cannula is assembled over the needle. A follower pin projects radially inwardly from the surface of the internal cavity in the cannula hub, and into the guide groove. When the needle is first inserted into the cannula, the follower pin moves to the rearward, or proximal, end of the first segment of the guide groove. In this position, the cannula is "locked" in place longitudinally, in that it is prevented from moving rearwardly, in purely longitudinal motion relative to the needle. This assists in insertion of the needle and cannula as a unit into the affected area of the patient.

When the distal end of the biopsy tool has been inserted to the affected area, the hub of the cannula is rotated relative to the needle, causing the follower pin to follow the second segment of the guide groove, which causes the cannula to partially withdraw from coverage of the needle. The lateral opening in the needle remains covered, however. This rotation of the hub also positions the follower pin at the forward, or distal end of the third segment of the guide groove. In this position, the cannula is "unlocked" longitudinally, in that it can be moved rearwardly, in purely longitudinal motion relative to the needle. When desired, the cannula can be withdrawn rearwardly from the needle, exposing the lateral opening.

The distal end of the needle, which can be radiopaque for ease of radiographic viewing, can be maneuvered to place a tissue sample in the lateral opening. The cannula can then be advanced forwardly, toward the distal end of the needle, to cut off the sample inside the needle, and to block the lateral opening. The distal end of the needle can then be placed in a saline solution, and the cannula withdrawn to expose the lateral opening to the solution. Once the lateral opening is exposed, the plunger latch can be released by the same hand in which the tool is held, and the plunger will move rearwardly under spring pressure. This full stroke of the plunger will quickly and uniformly draw the tissue sample and a quantity of saline solution into the syringe barrel. The physician can visually inspect the tissue sample, remove and plug the syringe, and send the pre-labelled syringe for subsequent analysis.

The novel features of this invention, as well as the invention itself, both as to its structure and its operation, will be best understood from the accompanying drawings, taken in conjunction with the accompanying description, in which similar reference characters refer to similar parts, and in which:

BRIEF DESCRIPTION OF THE DRAWINGS

FIG. 1 is a partial section view of the biopsy tool of the present invention, showing the cannula assembled onto the needle and locked longitudinally for insertion into the patient;

FIG. 2 is an elevation view of the syringe and needle shown in FIG. 1, with the plunger latched in the fully inserted position;

FIG. 3 is a section view of the cannula shown in FIG. 1;

FIG. 4 is a partial section view of the biopsy tool shown in FIG. 1, with the cannula in the longitudinally unlocked position;

FIG. 5 is a partial section view of the biopsy tool shown in FIG. 1, with the cannula withdrawn, exposing the lateral opening in the needle; and FIG. 6 is a partial section view of the biopsy tool shown in FIG. 1, with the plunger latch released and the plunger in the withdrawn position.

DESCRIPTION OF PREFERRED EMBODIMENTS

As seen in FIG. 1, biopsy tool 10 includes generally syringe 12, hollow cannula 14, and hollow needle 16. The distal end 26 of needle 16 is solid or plugged. The proximal end of needle 16 is mounted to the distal end of hollow locking barrel 18. The proximal end of locking barrel 18 is attached to the distal end of syringe 12. Cannula 14 is mounted coaxially over needle 16 with locking barrel 18 partially inserted within cannula 14.

Syringe 12, shown in FIG. 2, has a plunger 22 slidably mounted within syringe barrel 20 to move fluid into or out of syringe barrel 20. Syringe plunger 22 is biased outwardly from syringe barrel 20, or rearwardly, by plunger spring 58. Plunger spring 58 is mounted in compression between barrel flange 36, on the proximal end of syringe barrel 20, and plunger flange 38, on the proximal end of plunger 22. Plunger 22 is held fully inserted within syringe barrel 20, with plunger spring 58 fully compressed, by plunger latch 24, which is mounted on syringe barrel 20. Plunger latch 24 has a latch pivot 40 pressed against the distal side of barrel flange 36 and a latch finger 42 pressed against the proximal side of plunger flange 38, to hold plunger 22 inserted within syringe barrel 20. Pivoting of plunger latch 24 about latch pivot 40 results in the rotating of latch finger 42 out of engagement with plunger flange 38, allowing plunger spring 58 to expand, withdrawing plunger 22 from syringe barrel 20.

A female luer lock 34 is formed on the distal end of syringe barrel 20, for engagement with male luer lock 32 formed on the proximal end of locking barrel 18, releasably attaching syringe 12 to locking barrel 18. Locking barrel 18 has three groove segments formed into its outer surface, for use in controlling the relative positions of cannula 14 and needle 16, as will be explained later. Alignment groove 29 is a straight groove extending from the distal end of locking barrel 18 longitudinally along the outer surface of locking barrel 18 a relatively short distance. Alignment groove 29 accomplishes the initial alignment of cannula 14 with needle 16.

Guide groove 30 is a helical shaped groove extending from the proximal end of alignment groove 29 to a point half way around the outer surface of locking barrel 18. Guide groove 30 accomplishes the partial withdrawal of cannula 14 from needle 16, as cannula 14 is rotated relative to needle 16. Guide groove 30 also enables the longitudinal withdrawal of cannula 14 from needle 16, as will be explained later. Withdrawal groove 31 is a straight groove extending from the proximal end of guide groove 30 longitudinally along the outer surface of locking barrel 18. Withdrawal groove 31 guides cannula 14 longitudinally as cannula 14 is withdrawn from needle 16.

Needle 16 is a hollow steel tube having a solid or plugged distal end 26, which is cut at an angle to provide a sharp edge or point for ease of entry into the sample area. Lateral opening 28 is formed in the wall of needle 16, preferably near the distal end 26 of needle 16. Lateral opening 28 is formed with at least one sharp cutting edge 27 near the distal end of opening 28, to assist in the cutting of a sample from the selected tissue.

As seen in FIG. 3, cannula 14 consists of a hollow steel cannula tube 44, which has an open distal end 56 cut at an angle to match the angle on the distal end 26 of needle 16. Distal end 56 of cannula tube 44 has a sharp cutting edge to assist in cutting a sample from the selected tissue. Cannula bore 54 is sized to fit over needle 16 in a sliding relationship. The proximal end of cannula tube 44 is attached to cannula hub 46. Cavity 50 inside cannula hub 46 is a cylindrical cavity sized to fit over cylindrical locking barrel 18 in a sliding relationship. Follower pin 52 projects inwardly from cannula hub 46, into cavity 50. Follower pin 52 is of a length and diameter that will allow it to project into grooves 29, 30, 31 on the outer surface of locking barrel 18. Cannula hub 46 is formed with an outwardly projecting hub flange 48 to facilitate the rotation and withdrawal of cannula 14 relative to needle 16.

OPERATION

The operation of the biopsy tool of the present invention will now be described. The syringe barrel is first labelled with patient identification and other pertinent information. Plunger 22 is then fully inserted into syringe barrel 20, compressing spring 58, and plunger 22 is locked in the inserted position by rotating latch 24 until latch finger 42 presses against plunger flange 38. Needle 16 is attached to syringe 12 by attaching male luer lock 32 to female luer lock 34. Plunger insertion can alternatively take place after needle assembly, using saline solution to eliminate air pockets, as required.

Needle 16 is inserted through cannula hub 46 and into cannula tube 44, aligning follower pin 52 with alignment groove 29. Cannula 14 is pulled onto locking barrel 18 and needle 16 until follower pin 52 reaches the proximal end of alignment groove 29, as shown in FIG. 1. Cannula tube 44 is of such a length that cannula distal end 56 now aligns with needle distal end 26. The tool 10 is now configured for insertion to the desired sample area, into the tissue to be sampled, as a trocar. Since follower pin 52 is at the proximal end of alignment groove 29, cannula 14 can not be pushed further back along needle 16 as needle 16 is inserted to the sample area. Therefore, cannula 14 is locked against purely longitudinal motion further along needle 16. While holding the cannula hub 46 in place on the locking barrel 18, insert the tip of cannula 14 into the tissue to be sampled.

When the distal end of needle 16 has been inserted into the selected tissue, and while holding the syringe stationary, cannula hub 46 is rotated relative to locking barrel 18, causing follower pin 52 to follow helical guide groove 30 to the proximal end of helical guide groove 30, as shown in FIG. 4. This partially withdraws cannula 14 from needle 16, but lateral opening 28 in needle 16 is still covered by cannula tube 44. More importantly, cannula 14 is now positioned so that follower pin 52 is located at the distal end of withdrawal groove 31, so cannula 14 is now free to be withdrawn straight back along needle 16, to expose lateral opening 28. Therefore, cannula 14 is no longer locked against purely longitudinal motion further along needle 16.

While holding the syringe stationary, the physician can now pull on hub flange 48 to withdraw cannula 14 from needle 16, until follower pin 52 reaches the proximal end of withdrawal groove 31, as shown in FIG. 5. This exposes lateral opening 28 to the selected tissue. The physician can maneuver the distal end of needle 16, which can be radiopaque for ease of viewing, to place a sample of the tissue within opening 28 of needle 16. Cannula hub 46 is then pushed forward along locking barrel 18, to the position shown in FIG. 4, covering opening 28 and cutting a sample of the tissue off inside needle 16. With lateral opening 28 blocked, the tip of the biopsy tool 10 can be relocated to a saline solution or other desired fluid, if necessary. Cannula hub 46 is then again withdrawn to the fully retracted position shown in FIG. 5, exposing opening 28 to the fluid, and plunger latch 24 is pivoted to release plunger 22, as shown in FIG. 6, either by lifting latch finger 42 or by pressing down on the forward end of latch 24. Spring 58 then expands to withdraw plunger 22 fully from syringe barrel 20, drawing the tissue sample and fluid into syringe barrel 20.

The physician can then visually examine the sample and repeat the sample procedure, if necessary, without withdrawing the needle from the sample area. This can significantly reduce the trauma to the patient. Once a satisfactory sample is obtained, the physician can withdraw the needle from the patient, remove the syringe from the locking barrel, plug the syringe, and set aside the syringe for later analysis.

While the particular biopsy tool as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

We claim:

1. A biopsy tool, comprising:
   a hollow needle, said needle having a closed distal end;
   a lateral opening in said needle;
   a hollow cannula coaxially mountable to said needle for selective purely longitudinal movement relative to said needle to block said lateral opening;
   locking means for locking said cannula against pure longitudinal movement relative to said needle; and
   suction means connectable to said needle;
   wherein said locking means locks said cannula by rotational movement of said cannula relative to said needle.

2. A biopsy tool as claimed in claim 1, where said locking means comprises:
   a locking barrel mounted on a proximal end of said needle;
   a guide groove in a surface of said locking barrel; and
   a follower pin on said cannula, said pin being positioned for movement along said guide groove from a first position where said cannula is locked, to a second position where said cannula is unlocked, for pure longitudinal movement relative to said needle.

3. A biopsy tool as claimed in claim 1, further comprising a sharp edge on said cannula for cutting any tissue extending through said lateral opening, when said cannula is moved to block said lateral opening.

4. A biopsy tool as claimed in claim 3, wherein said sharp edge aligns with said distal end of said needle to promote ease of insertion into a patient.

5. A biopsy tool as claimed in claim 1, wherein said suction means comprises a syringe having a plunger.

6. A biopsy tool, comprising:
a hollow needle, said needle having a closed distal end;
a lateral opening in said needle;
a hollow cannula coaxially mountable to said needle for selective movement relative to said needle to block said lateral opening;
a syringe connectable to said needle, said syringe having a plunger;
a locking barrel mounted on a proximal end of said needle;
a male luer lock on said locking barrel;
a female luer lock on said syringe; and
a selectively releasable latch mounted on said syringe to hold said plunger in an inserted position within said syringe.

7. A biopsy tool as claimed in claim 6, further comprising biasing means for biasing said plunger toward a withdrawn position.

8. A biopsy tool, comprising:
a hollow needle, said needle having a closed distal end;
a lateral opening in said needle, near said distal end of said needle;
a locking barrel coaxially mountable on a proximal end of said needle;
a hollow cannula coaxially mountable on the exterior of said needle and said locking barrel, for selective movement relative to said needle to block said lateral opening;
a guide groove on an exterior surface of said locking barrel;
a follower pin projecting radially inwardly from an interior surface of said cannula, into said guide groove, for controlling the relative positions of said cannula and said needle; and
suction means connectable in fluid communication with said needle.

9. A biopsy tool as claimed in claim 8, wherein:
said selective movement of said cannula is longitudinal relative to said needle;
said follower pin moves from a first position in said guide groove to a second position in said guide groove;
when said follower pin is in said first position, said cannula is prevented from purely longitudinal movement relative to said needle; and
when said follower pin is in said second position, said cannula is allowed to have purely longitudinal movement relative to said needle.

10. A biopsy tool as claimed in claim 8, wherein said suction means comprises a syringe having a plunger within a barrel, 11. A biopsy tool as claimed in claim 10, further comprising biasing means for biasing said plunger toward a position withdrawn from said barrel of said syringe.

12. A method for taking a biopsy sample of tissue, comprising the steps of:
providing a hollow needle, said needle having a closed distal end and a lateral opening near said distal end;
coaxially mounting a hollow cannula on said needle so as to block said lateral opening;
inserting said distal end of said needle and said cannula into the tissue to be sampled;
moving said cannula relative to said needle to expose said lateral opening to the tissue;
maneuvering said distal end of said needle to place the sample of tissue inside said needle through said lateral opening;
moving said cannula relative to said needle to cut the sample from the tissue;
attaching a syringe to said needle, said syringe having a plunger which is spring biased toward a withdrawn position, said syringe also having a selectively releasable latch holding said plunger in an inserted position; and
releasing said latch to allow said plunger to move toward said withdrawn position, thereby drawing a suction on said needle.

13. A method as claimed in claim 12, wherein said step of moving said cannula to expose said lateral opening is a longitudinal movement.

14. A method as claimed in claim 12, wherein said step of moving said cannula to cut the sample is a longitudinal movement.

15. A method for taking a biopsy sample of tissue, comprising the steps of:
providing a hollow needle, said needle having a closed distal end and a lateral opening near said distal end;
attaching a syringe to said needle, said syringe having a plunger which is latched in a first position inserted in a barrel of said syringe by a selectively releasable latch, and said syringe having a biasing means for biasing said plunger toward a second position withdrawn from said syringe barrel;
coaxially mounting a hollow cannula on said needle so as to block said lateral opening;
locking said cannula against longitudinal movement relative to said needle, with a distal end of said cannula aligned with said distal end of said needle;
inserting said distal end of said needle and said cannula into the tissue to be sampled;
unlocking said cannula to allow longitudinal movement relative to said needle;
withdrawing said cannula longitudinally relative to said needle to expose said lateral opening to the tissue;
maneuvering said distal end of said needle to place the sample of tissue inside said needle through said lateral opening;
advancing said cannula longitudinally relative to said needle to cut the sample from the tissue;
positioning said distal end of said needle in a fluid;
withdrawing said cannula longitudinally relative to said needle to expose said lateral opening to the fluid; and
releasing said latch to allow said plunger to move toward said withdrawn position to draw the sample into said syringe.

* * * * *